United States Patent [19]
Gauthier et al.

[11] Patent Number: 5,672,586
[45] Date of Patent: Sep. 30, 1997

[54] HERPES RIBONUCLEOTIDE REDUCTASE INHIBITORS

[75] Inventors: Jean André Gauthier, Montréal, Canada; Neil Moss, Danbury, Conn.

[73] Assignee: Bio-Mega/Boehringer Ingelheim Research, Inc., Quebec, Canada

[21] Appl. No.: 666,732

[22] Filed: Jun. 18, 1996

[30] Foreign Application Priority Data

Jun. 23, 1995 [CA] Canada .................................. 2152541

[51] Int. Cl.⁶ .......................... A61K 38/04; A61K 38/07; C07K 5/00
[52] U.S. Cl. ........................... 514/18; 514/17; 530/330; 530/331; 530/333
[58] Field of Search .................. 514/18, 17; 530/330, 530/331, 333

[56] References Cited

U.S. PATENT DOCUMENTS

| 4,795,740 | 1/1989 | Cohen et al. | 514/14 |
| 4,814,432 | 3/1989 | Freidinger et al. | 530/329 |
| 5,574,015 | 11/1996 | Beaulieu et al. | 514/18 |

FOREIGN PATENT DOCUMENTS

| 0411334 | 2/1991 | European Pat. Off. |
| 0412595 | 2/1991 | European Pat. Off. |
| 0560267 | 9/1993 | European Pat. Off. |
| 0618226 | 10/1994 | European Pat. Off. |
| WO9420528 | 2/1994 | WIPO |

OTHER PUBLICATIONS

R.E. Boehme et al., Chapter 15, Antiviral Agents in "Annual Reports in Medicinal Chemistry", 29, pp. 145–154 (1994).

P. Gaudreau et al., "Synthesis and Inhibitory Potency of Peptides Corresponding to the Subunit 2 C-Terminal Region of Herpes Virus Ribonucleotide Reductases", *J. Med. Chem.*, pp. 723–730 (1990).

L.L. Chang et al. "Substituted Penta–and Hexapeptides as Potent Inhibitors of Herpes Simplex Virus Type 2 Ribonucleotide Reductase", *Bioorganic and Medicinal Chemistry Letters*, pp. 1207–1212 (1992).

N. Moss et al., "Inhibition of Herpes Simplex Virus Type 1 Ribonucleotide Reductase by Substituted Tetrapeptide Derivatives", *J. Med. Chem.*, pp. 3005–3009 (1993).

*Primary Examiner*—Cecilia J. Tsang
*Assistant Examiner*—Bennett Celsa
*Attorney, Agent, or Firm*—Robert P. Raymond; Alan R. Stempel; Wendy E. Rieder

[57] ABSTRACT

Disclosed herein are compounds of the formula

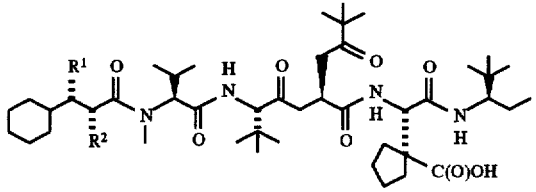

wherein $R^1$ is hydrogen or (1–4C) alkyl, $R^2$ is (1–4C) alkyl or a therapeutically acceptable salt thereof. The compounds are useful for treating herpes infections.

22 Claims, 1 Drawing Sheet

HERPES RIBONUCLEOTIDE REDUCTASE INHIBITORS

FIELD OF INVENTION

This invention relates to peptidomimetic compounds having antiviral properties and to means for using the compounds to treat viral infections. More specifically, the invention relates to peptidomimetic compounds exhibiting activity against herpes viruses, to pharmaceutical compositions comprising the compounds, and to methods of using the compounds to inhibit the replication of herpes virus and to treat herpes infections.

BACKGROUND OF THE INVENTION

Herpes viruses inflict a wide range of diseases against humans and animals. For instance, herpes simplex viruses, types 1 and 2 (HSV-1 and HSV-2), are responsible for cold sores and genital lesions, respectively; varicella zoster virus (VZV) causes chicken pox and shingles; and the Epstein-Barr virus (EBV) causes infectious mononucleosis.

Over the past two decades, a class of compounds known as the purine and pyrimidine nucleoside analogs has received the most attention by investigators in the search for new therapeutic agents for treatment of herpes virus infections. As a result, several nucleoside analogs have been developed as antiviral agents. The most successful to date is acyclovir which is the agent of choice for treating genital herpes simplex infections.

Nevertheless, in spite of some significant advances, the need for effective, safe therapeutic agents for treating herpes viral infections continues to exist. For a review of current therapeutic agents in this area, see R. E. Boehme et al., Annual Reports in Medicinal Chemistry, 29, 145 (1994).

The present application discloses a group of compounds having activity against herpes simplex viruses. The selective action of these compounds against herpes viruses, combined with a wide margin of safety, renders the compounds as desirable agents for combating herpes infections.

The following references disclose peptides or peptidomimetic compounds which have been associated with antiherpes activity:

E. A. Cohen et al., U.S. Pat. No. 4,795,740, Jan. 3, 1989,
R. Freidinger et al., U.S. Pat. No. 4,814,432, Mar. 21, 1989,
P. Gaudreau et al., J. Med. Chem., 33, 723 (1990),
J. Adams et al., European patent application 411,334, published Feb. 6, 1991,
R. L. Tolman et al., European patent application 412,595, published Feb. 13, 1991,
L. L. Chang et al., Bioorganic & Medicinal Chemistry Letters, 2, 1207 (1992),
P. L. Beaulieu et al., European patent application 560,267, published Sep. 15, 1993,
N. Moss et al., J. Med. Chem., 36, 3005 (1993), and R. Déziel and N. Moss, European patent application 618, 226, published Oct. 5, 1994.

The subject peptides of the previous reports can be distinguished from the peptides of the present application by characteristic structural and biological differences.

Abbreviations and symbols used hereinafter are defined in "Details of the Invention" section of this application.

SUMMARY OF THE INVENTION

The compounds of this invention are represented by formula 1 wherein $R^1$ is hydrogen or (1–4C)alkyl and $R^2$ is (1–4C) alkyl; or a therapeutically acceptable salt thereof.

A preferred group of the compounds of this invention are represented by formula 1 wherein $R^1$ is hydrogen or methyl and $R^2$ is methyl, ethyl, 1-methylethyl or propyl; or a therapeutically acceptable salt thereof.

A more preferred group of the compounds are represented by formula 1 wherein $R^1$ is hydrogen and $R^2$ is methyl, ethyl or 1-methylethyl; or a therapeutically acceptable salt thereof.

Included within the scope of this invention is a pharmaceutical composition comprising an antiherpes virally effective amount of a compound of formula 1, or a therapeutically acceptable salt thereof, and a pharmaceutically acceptable carrier.

Also included within the scope of this invention is a cosmetic composition comprising a compound of formula 1, or a therapeutically acceptable salt thereof, and a physiologically acceptable carrier suitable for topical application.

An important aspect of the invention involves a method of treating a herpes viral infection in a mammal by administering to the mammal an anti-herpes virally effective amount of the compound of formula 1, or a therapeutically acceptable salt thereof.

Another important aspect involves a method of inhibiting the replication of herpes virus by contacting the virus with a herpes viral ribonucleotide reductase inhibiting amount of the compound of formula 1, or a therapeutically acceptable salt thereof.

Still another aspect involves a method of treating a herpes viral infection in a mammal by administering thereto an antiherpes virally effective amount of a combination of the compound of formula 1, or a therapeutically acceptable salt thereof, and an antiviral nucleoside analog. A pharmaceutical composition comprising the combination is also within the scope of this invention.

Processes for preparing the compounds of formula 1 are described hereinafter.

DETAILS OF THE INVENTION

General

Figure 1:
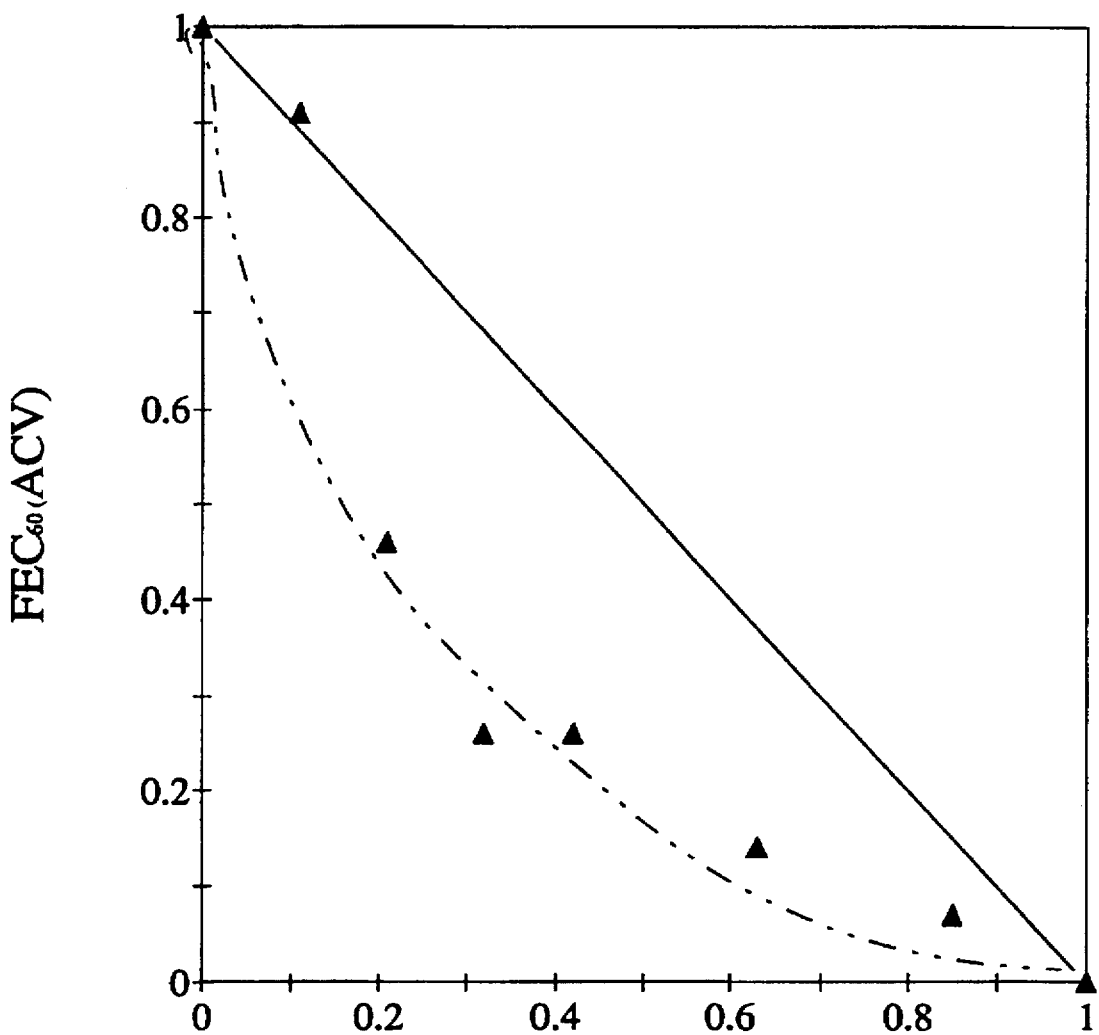
FIG. 1 is a graphical representation of results obtained from studies involving combinations of acyclovir and a peptidomimetic compound of formula 1. The studies involve the application of the isobole method, described in example 12, to demonstrate the synergistic activity of the combinations against herpes simplex virus, type 1. See example 12 for details.

Alternatively, formula 1 can be illustrated as:

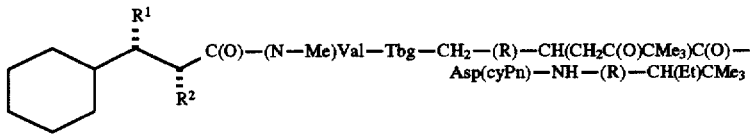

wherein (N-Me)Val represents the amino acid residue of (S)-2-(methylamino)-3-methylbutanoic acid, Tbg represents the amino acid residue of (S)-2-amino-3,3-dimethylbutanoic acid, Me and Et represent the alkyl radicals methyl and ethyl, respectively, and Asp(cyPn) represents the amino acid residue of (S)-α-amino-1-carboxycyclo-pentaneacetic acid.

The term "residue" with reference to an amino acid or amino acid derivative means a radical derived from the corresponding α-amino acid by eliminating the hydroxyl of the carboxy group and one hydrogen of the α-amino group.

The term "(1–4C)alkyl" as used herein means an alkyl radical containing from one to four carbon atoms and includes methyl, ethyl, propyl, 1-methylethyl, 1,1-dimethylethyl and butyl.

The term "pharmaceutically acceptable carrier" as used herein means a non-toxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "effective amount" means a predetermined antiviral amount of the antiviral agent, i.e. an amount of the agent sufficient to be effective against herpes virus in vivo.

Process for Preparing the Compounds of Formula 1

In general, the compounds of formula 1 are prepared by known methods using reaction conditions which are known to be suitable for the reactants. Description of the methods are found in standard textbooks such as "Annual Reports In Organic Synthesis—1994", P. M. Weintraub et al., Eds, Academic Press, Inc., San Diego, Calif., U.S.A., 1994 (and the preceding annual reports), "Vogel's Textbook Of Practical Organic Chemistry", B. S. Furniss et al., Eds, Longman Group Limited, Essex, UK, 1986, and "Comprehensive Organic Synthesis", B. M. Trost and I. Fleming, Eds, Pergaman Press, Oxford, UK, 1991, Volumes 1 to 8.

An exception to the latter statement, however, is the unique stereospecific synthesis of a key intermediate for the preparation of the compounds of formula 1. This key intermediate is represented by formula 2

$$W^1\text{-Tbg-CH}_2\text{—(R)—CH(CH}_2\text{C(O)CMe}_3\text{)C(O)OW}^2 \qquad (2)$$

wherein $W^1$ is an amino protective group, and $W^2$ is a carboxyl protective group. In this instance, $W^2$ is a protective group which can be selectively removed in the presence of the protective group $W^1$. Preferably, $W^1$ is tert-butyloxycarbonyl (Boc) or 2,2,2-trichloroethoxycarbonyl and $W^2$ is benzyl, (4-nitrophenyl)methyl, methyl or ethyl.

The intermediate of formula 2 can be prepared by a stereospecific process illustrated in the following Scheme 1:

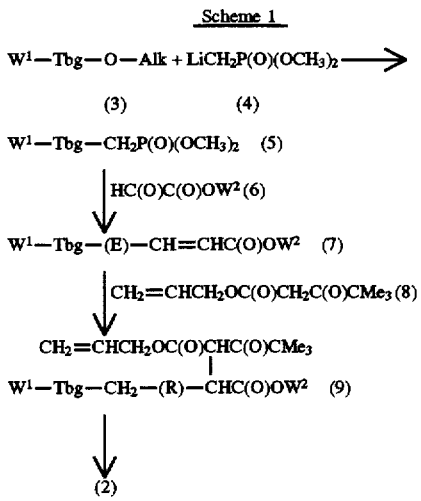

wherein $W^1$ and $W^2$ are as defined herein and Alk is methyl or ethyl.

With reference to the preceding schematic representation, a starting material of formula $W^1$-Tbg-O-Alk (3) is reacted with the reagent $LiCH_2P(O)(OCH_3)_2$(4) (prepared from $CH_3P(O)(OCH_3)_2$ and butyllithium) to give a phosphonate of formula $W^1$-Tbg-$CH_2P(O)(OCH_3)_2$ (5). Reaction of the latter phosphonate with a glyoxylyl ester of formula HC(O)C(O)OW$^2$(6) in the presence a suitable tertiary amine, preferably triethylamine or diisopropylethylamine, affords a γ-keto-α,β-unsaturated ester of formula $W^1$-Tbg-(E)-CH=CHC(O)OW$^2$ (7). Reaction of the latter compound with the sodium enolate of a β-ketoester of formula $CH_2$=CHCH$_2$OC(O)CH$_2$C(O)CMe$_3$(8) affords a Michael adduct of formula $W^1$-Tbg-CH$_2$—(R)—CH{CH (C(O)CMe$_3$)-(C(O)OCH$_2$CH=CH$_2$)}C(O)OW$^2$(9).

Note (1): The β-ketoester of formula 8, i.e. $CH_2$=CHCH$_2$OC(O)CH$_2$C(O)CMe$_3$, is prepared readily by reacting the lithium enolate of allyl acetate with trimethylacetyl chloride.

Note (2): The sodium enolate of the β-ketoester of formula 8 is generated in situ from the β-ketoester in the presence of a catalytically effective amount of sodium hydride.

Thereafter, reaction of the Michael adduct of formula 9 with tetrakistriphenylphosphine palladium(O) in the presence of a suitable secondary amine, preferably pyrrolidine or piperidine, similar to the method of R. Déziel, Tetrahedron Letters, 28, 4371 (1987), effects deallylation and subsequent decarboxylation of the allyl ester to give the key intermediate of formula 2.

Noteworthy is the unexpected high stereo-selectivity obtained in the Michael addition reaction of the γ-keto-α, β-unsaturated ester of formula 7 with the sodium enolate of the β-ketoester of formula 8 to give the Michael adduct of formula 9. The stereoselectivity of the Michael addition reaction is inferred by the fact that the intermediate of formula 2, derived directly from the Michael adduct, is obtained essentially as a single isomer. The diastereoisomeric purity of the intermediate of formula 2 can be demonstrated by nuclear magnetic resonance studies. The enantiomeric purity of the intermediate of formula 2 can be assessed by removing the amino protective group ($W^1$) and applying the method of J. A. Dale et al., J. Org. Chem., 34, 2543 (1969) to the resulting free amino derivative (see example 4 for more detail).

Thereafter again, the carboxyl protective group ($W^2$) of the key intermediate of formula 2 is selectively removed by standard methods, for example, by hydrogenolysis in the instance wherein $W^2$ is benzyl, to give the corresponding free carboxylic acid derivative (see formula 14 in Scheme 2 below ) for incorporation into the process for preparing the compounds of formula 1 .

In general, the incorporation of the preceding free carboxylic acid derivative into a process for the preparation of the compounds of formula 1 can be envisaged as a sequence of chemical events wherein a carboxylic acid derivative (representing a first unit) is joined to two other units by forming amide bonds.

In the following more detailed description of a convenient and practical process for preparing the compounds of formula 1, a certain order of the chemical events is followed. However, it will be appreciated that changes in the order of chemical events are not critical and therefore such changes are deemed to be within the scope of the present invention.

Likewise, it should be appreciated that the intermediate of formula 2 wherein protective group $W^1$ can be selectively removed in the presence of protective group $W^2$, allowing for a change in the order of the chemical events, also is deemed to be within the scope of the present invention. Accordingly, an important aspect of this invention includes a key intermediate of formula 2 in which $W^1$ is an amino protective group for the amine at the N-terminus and $W^2$ is a carboxyl protective group for the carboxyl at the C-terminus of the intermediate, with the proviso that the amino protective group $W^1$ can be selectively removed in the presence of the carboxyl protective group $W^2$ when the terminal amine is destined for the reaction to follow, or that, on the other hand, the carboxyl protective group $W^2$ can be selectively removed in the presence of the amino protective group $W^1$ when the terminal carboxyl is destined for the reaction to follow.

Examples of the intermediates of formula 2 wherein the amino protective group $W^1$ can be selectively removed in the presence of the carboxyl protective group $W^2$ include those in which $W^1$ is tert-butyloxycarbonyl and $W^2$ is benzyl, 2,2,2-trichloroethyl, methyl or ethyl.

More particularly, with respect to an overall process, the compounds of formula 1 can be prepared by a convenient and practical process illustrated in the following Scheme 2.

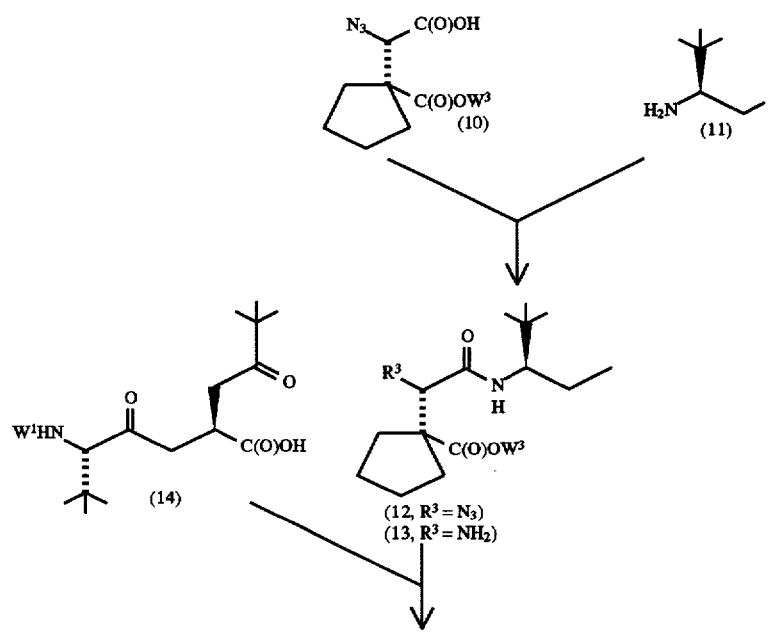

-continued
Scheme 2

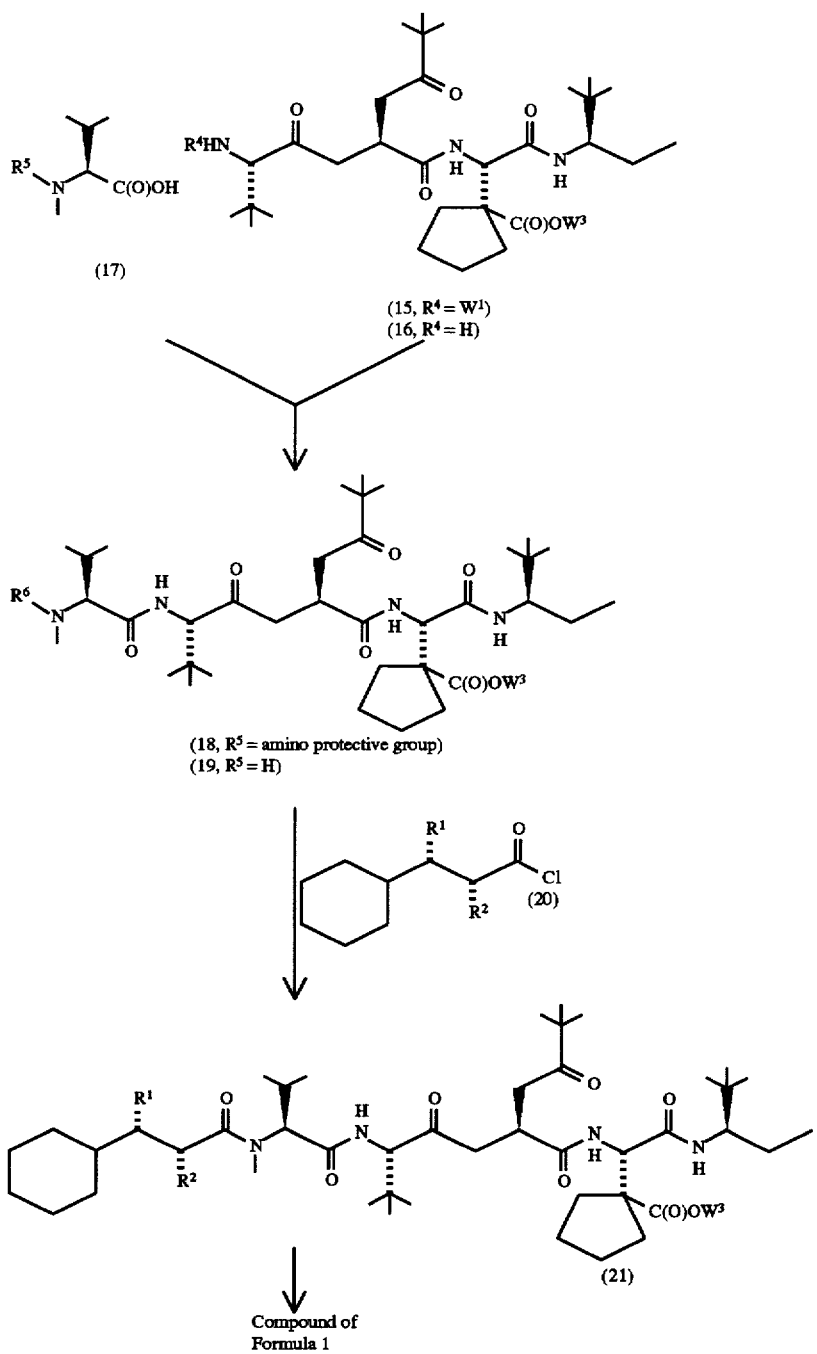

In Scheme 2, $W^1$ is as defined herein, $W^3$ is a carboxyl protective group (preferably benzyl, tert-butyl or 2,2,2-trichloroethyl), $R^3$ is azido for formula 12 and an amino for formula 13, $R^4$ is $W^1$ as defined herein for formula 15 and a hydrogen for formula 16, $R^5$ is an amino protective group preferably tert-butyloxycarbonyl or 2,2,2-trichloroethoxycarbonyl, for the compounds of formula 17 and 18, and a hydrogen for formula 19, and $R^1$ and $R^2$ are as defined herein.

Referring to Scheme 2, a process for preparing compound of formula 1 comprises:

(a) coupling a carboxylic acid derivative of formula 10 with an amine of formula 11 to obtain an α-azidoamide of formula 12,
(b) reducing the α-azidoamide of formula 12 to obtain a corresponding α-aminoamide of formula 13,
(c) coupling the α-aminoamide of formula 13 with a carboxylic acid derivative of formula 14 to obtain a diprotected intermediate of formula 15,
(d) selectively deprotecting the diprotected intermediate of formula 15 to obtain a free N-terminal derivative of formula 16, (e) coupling the free N-terminal derivative of formula 16 with an N-protected valine of formula 17 to obtain a diprotected intermediate of formula 18, (f) selectively deprotecting the latter diprotected intermediate of formula 18 to obtain a corresponding free N-terminal compound of formula 19, (g) reacting the free N-terminal compound of formula 19 with an acid chloride of formula 20 to obtain a corresponding protected carboxyl derivative of formula 21, and (h) deprotecting the latter derivative of formula 21 to obtain the corresponding compound of formula 1, and (i) if desired transforming the compound of formula 1 into a therapeutically acceptable salt thereof.

The coupling steps (a), (c) and (e) and the deprotecting steps (d), (f) and (h) can be achieved by methods commonly used in peptide synthesis.

More explicitly, the coupling step involves the dehydrative coupling of a free carboxyl of one reactant with the free amino group of the other reactant in the presence of coupling agent to form a linking amide bond. Description of such coupling agents are found in general textbooks on peptide chemistry, for example, M. Bodanszky, "Peptide Chemistry", 2nd rev ed, Springer-Verlag, Berlin, Germany, 1993. Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A very practical and useful coupling agent is the commercially available (benzotriazol-1-yloxy) tri-(dimethylamino) phosphonium hexafluorophosphate, either by itself or in the presence of 1-hydroxybenzotriazole. Still another very practical and useful coupling agent is commercially available 2-(1H-benzotriazol-1-yl)-N, N, N', N'-tetramethyluronium tetrafluoroborate.

The coupling reaction is conducted in an inert solvent, e.g. dichloromethane or acetonitrile. An excess of a tertiary amine, e.g. diisopropylethylamine or N-methylmorpholine, is added to maintain the reaction mixture at a pH of about eight. The reaction temperature usually ranges between 0° and 50 ° C. and the reaction time usually ranges between 15 minutes and 24 hours.

In step (b), the azide group of the α-azidoamide of formula 12 is transformed into a corresponding amine of the α-aminoamide of formula 13 by a reducing agent capable of selectively reducing an azide to an amino group in the presence of an amido group and an ester group. This step can be accomplished conveniently and efficiently by the method of N. Maiti et al., Tetrahedron Letters, 27, 1423 (1986) using stannous chloride as the reducing agent and methanol as the reaction solvent.

In step (g), the free N-terminal compound of formula 19 is reacted directly with 1 to 1.5 molar equivalents of the acid chloride of formula 20 to give the protected carboxyl derivative of formula 21. This step is based on the classical method for preparing amides whereby an acid chloride is reacted with the terminal amino group. The reaction proceeds readily in the presence of an (1.2 to 2.0 molar equivalents) excess of a suitable tertiary amine, for example N-methylmorpholine or diisopropylethylamine. The reaction is conducted in an inert solvent, such as dichloromethane or toluene, and at temperatures usually ranging from −20 ° C. to 20 ° C.

Furthermore, if desired, the compound of formula 1 can be obtained in the form of a therapeutically acceptable salt. Such salts can be considered as biological equivalents of the compounds of formula 1. Examples of such salts (of the carboxy group) are those formed by known methods with the sodium, potassium or calcium cation.

The acid chlorides of formula 20 are known or can be prepared readily by known methods. For illustration, simple procedures for the preparation of certain acid chlorides of formula 20 are included in the examples.

Antiherpes Activity

The antiviral activity of the compounds of formula 1 can be demonstrated by biochemical, microbiological and biological procedures showing the inhibitory effect of the compounds on the replication of herpes simplex viruses, types 1 and 2 (HSV-1 and HSV-2), as well as acyclovir-resistant herpes simplex viruses.

In the examples hereinafter, the inhibitory effect on herpes ribonucleotide reductase is noted for exemplary compounds of formula 1. Noteworthy, in the connection with this specific inhibition of herpes ribonucleotide reductase, is the relatively minimal effect or absence of such an effect of the compounds on cellular ribonucleotide reductase activity required for normal cell replication.

A method for demonstrating the inhibitory effect of the compounds of formula 1 on viral replication is the cell culture technique; see, for example, T. Spector et al., Proc. Natl. Acad. Sci. U.S.A., 82, 4254 (1985).

The therapeutic effect of the compounds of formula 1 can be demonstrated in laboratory animals, for instance, by using an assay based on the murine model of herpes simplex virus-induced ocular disease for antiviral drug testing, described by C. R. Brandt et al., J. Virol. Meth., 36, 209 (1992).

When a compound of this invention, or one of its therapeutically acceptable acid addition salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the compound, chosen route of administration and standard biological practice. For topical administration, the compound can be formulated in pharmaceutically accepted vehicles containing 0.1 to 5 percent, preferably 0.5 to 5 percent, of the active agent. Such formulations can be in the form of a solution, cream or lotion.

For systemic administration, the compound of formula 1 is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's Pharmaceutical Sciences", 18th ed, Mack Publishing Company, Easton, Pa., 1990.

The dosage of the compound will vary with the form of administration and the particular active agent chosen. Furthermore, it will vary with the particular host under treatment. Generally, treatment is initiated with small increments until the optimum effect under the circumstances is reached. In general, the compound is most desirably administered at a concentration level that will generally afford antivirally effective results without causing any harmful or deleterious side effects.

With reference to topical application, the compound of formula 1 is administered cutaneously in a suitable topical formulation to the infected area of the body e.g. the skin or part of the oral or genital cavity, in an amount sufficient to cover the infected area. The treatment should be repeated, for example, every four to six hours until lesions heal.

With reference to systemic administration, the compound of formula 1 is administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

Another aspect of this invention comprises a cosmetic composition comprising a herpes viral prophylactic amount of the compound of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the compound than corresponding pharmaceutical compositions for topical application. A preferred range of the amount of the compound in the cosmetic composition is 0.5 to 5 percent by weight.

Although the formulations disclosed hereinabove are indicated to be effective and relatively safe medications for treating herpes viral infections, the possible concurrent administration of these formulations with other antiviral medications or agents to obtain beneficial results is not excluded. Such other antiviral medications or agents include the antiviral nucleosides, for example, acyclovir, and antiviral surface active agents or antiviral interferons such as those disclosed by S. S. Asculai and F. Rapp in U.S. Pat. No. 4,507,281, Mar. 26, 1985.

More specifically with respect to treating herpes viral infections by concurrent administration, it has been found that the antiherpes activity of an antiviral nucleoside analogs can be enhanced synergistically, without the concomitant enhancement of toxic effects, by combining the same with a compound of formula 1. Accordingly, there is provided herewith a pharmaceutical composition for treating herpes infections in a mammal comprising a pharmaceutically acceptable carrier, and an effective amount of the combination of an antiviral nucleoside analog or a therapeutically acceptable salt thereof, and a ribonucleotide reductase inhibiting compound of formula 1 or a therapeutically acceptable salt thereof.

Also provided herein is a method of treating herpes viral infections in a mammal. The method comprises administering to the mammal an anti-herpes virally effective amount of a combination of a compound of formula 1 or a therapeutically acceptable salt thereof, and an antiviral nucleoside analog or a therapeutically acceptable salt thereof.

The antiviral nucleoside analog employed in the combination is one which is enzymatically convertible (in vivo) to a viral DNA polymerase inhibitor of, and/or an alternative substrate for, a herpes DNA polymerase. The antiviral nucleoside analog can be selected from known nucleoside analogs. Preferred nucleoside analogs of the invention include acyclovir and its analogs; for example, the compounds of formula 22

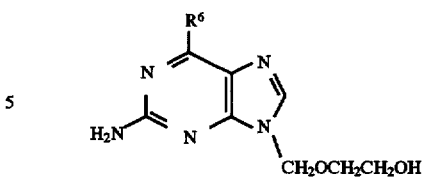

wherein $R^6$ is hydrogen, hydroxy or amino, or a therapeutically acceptable salt thereof. (Formula 22 wherein $R^6$ is hydroxy represents acyclovir.)

Other preferred antiviral nucleoside analogs for use according to the present invention include penciclovir, famciclovir and valacyclovir.

An example of a therapeutically acceptable salt of the nucleoside analogs is the sodium salt.

The term "synergistic effect" when used in relation to the antiviral or antiherpes activity of the above defined combination of the nucleoside analog and the compound of formula 1 means an antiviral or antiherpes effect which is greater than the predictive additive effect of the two individual components of the combination.

When utilizing the combination of this invention for treating herpes infections, the combination is administered to warm blooded animals, e.g. humans, pigs or horses, in a vehicle comprising one or more pharmaceutically acceptable carriers, the proportion of which is determined by the solubility and chemical nature of the nucleoside analog and the compound of formula 1, chosen route of administration, standard biological practice, and by the relative amounts of the two active ingredients to provide a synergistic antiviral effect. The combination may be administered topically. For example, the two active agents (i.e. the antiviral nucleoside analog and the compound of formula 1, or their therapeutically acceptable salts) can be formulated in the form of solutions, emulsions, creams, or lotions in pharmaceutically acceptable vehicles. Such formulation can contain 0.01 to 1.0 percent by weight of the nucleoside analog, or a therapeutically acceptable salt thereof, and about 0.05 to 1 percent by weight of the compound of formula 1, or a therapeutically acceptable salt thereof.

In any event, the two active agents are present in the pharmaceutical composition in amounts to provide a synergistic antiherpes effect.

The following examples illustrate further this invention. Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Abbreviations used in the examples include Boc: tert-butyloxycarbonyl; Bzl: benzyl; DMSO: dimethyl-sulfoxide; Et: ethyl; EtOH: ethanol; EtOAc: ethyl acetate; Et$_2$O: diethyl ether; HPLC: high performance liquid chromatography; Me: methyl; MeOH: methanol; Pr: propyl; TLC: thin layer chromatography; THF: tetrahydrofuran.

EXAMPLE 1

General Procedure for Coupling Reactions

{See also R. Knorr et al., Tetrahedron Letters, 30, 1927 (1989).}

The first reactant, i.e. a free amine (or its hydrochloride salt), is dissolved in CH$_2$Cl$_2$ or CH$_3$CN and the solution is cooled to 4°. Under a nitrogen atmosphere, four equivalents of N-methylmorpholine are added to the stirred solution.

After 20 min, one equivalent of the second reactant, i.e. a free carboxylic acid, and 1.05 equivalents of the coupling agent are added. (Practical and efficient coupling reagents for this purpose are (benzotriazol-1-yloxy) tris-(dimethylamino) phosphonium hexafluorophosphate or preferably 2-(1H-benzotriazol-1-yl)-N, N,N',N'-tetramethyluronium tetrafluoroborate. The reaction is monitored by TLC. After completion of the reaction, the solvent is evaporated under reduced pressure. The residue is dissolved in EtOAc. The solution is washed successively with 1 N aqueous citric acid, 10% aqueous $Na_2CO_3$ and brine. The organic phase is dried ($MgSO_4$), filtered and concentrated under reduced pressure. The residue is purified on silica gel ($SiO_2$) according to Still's flash chromatography technique {W. C. Still et al., J. Org. Chem., 43, 2923 (1978)}.

EXAMPLE 2

Preparation of 1(R)-Ethyl-2,2-dimethylpropylamine Hydrochloride (NH2—(R)—CH(Et)CMe$_3$.HCl).

To a cooled solution (0°) of 4,4-dimethyl-3-pentanone (106 g, 0.928 mol) and (R)-α-methylbenzylamine (111 g, 0.916 mol) in benzene (1 L), a solution of $TiCl_4$ (50.5 mL, 0.461 mol) in benzene (200 mL) was added at a rate that kept the temperature of the mixture below 10°. Thereafter, the mixture was stirred mechanically for 3 h at 40°, cooled to room temperature (20°–22°) and filtered through diatomaceous earth. The diatomaceous earth was washed with $Et_2O$. The combined filtrate and wash was concentrated. The residue was dissolved in dry MeOH (2 L). The solution was cooled to 0° and $NaBH_4$ (20 g, 0.53 mol) was added portionwise while maintaining the temperature of the mixture below 5°. The methanol was evaporated. The residue was dissolved in $Et_2O$. The solution was washed with brine, dried ($MgSO_4$) and concentrated to give a reddish oil (a 18:1 mixture of diastereoisomers as indicated by NMR). The oil was purified by flash chromatography ($SiO_2$, eluent: EtOAc/hexane, 7:93) to afford N-(1(R)-phenylethyl)-1(R)-ethyl-2, 2-dimethylpropylamine as a liquid (110 g, 54% yield). This material was dissolved in hexane (1.5 L). 1N HCl in $E_2O$ (550 mL) was added to the solution over a period of 15 min. The resulting white solid was collected on a filter and then washed with hexane to provide N-(1(R)-phenylethyl)-1(R)-ethyl-2,2-dimethylpropylamine hydrochloride (125 g, 97% yield). $^1$H NMR(CDCl$_3$) δ7.79–7.74 (m, 2H), 7.48–7.30 (m, 3H), 4.49–4.31 (m, 1H), 2.44–2.36 (m, 1H), 2.23 (d, J=6.5 Hz, 3H), 1.95–1.54 (m, 2H), 1.14 (s, 9H), 0.55 (t, J=7.5 Hz, 3H).

A solution of the latter compound (41.5 g) in MeOH (120 mL) was mixed with 10% Pd/C (w/w) (4.2 g) and the mixture was shaken under 50 psi of hydrogen in a Parr hydrogenator at room temperature for 48 h. The mixture was filtered through diatomaceous earth and the filtrate was concentrated to give the desired NH$_2$—(R)—CH(Et)CMe$_3$ in the form of its hydrochloric acid addition salt, as a white solid (25 g, 100% yield). $^1$H NMR(CDCl$_3$) δ 8.40–8.10 (broad s, 3H), 2.85–2.70 (m, 1H), 1.90–1.58 (m, 2H), 1.22 (t, J=7 Hz, 3H), 1.10 (s, 9H).

EXAMPLE 3

Preparation of the Intermediate H-Asp(cyPn)(Bzl) —NH—(R)—CH (Et)CMe$_3$ (the compound of formula 13 wherein $R^4$ is NH$_2$ and $W^3$ is Bzl)

(a) (S)-α-Azido-1-{(phenylmethoxy)carbonyl}cyclopentaneacetic acid (the compound of formula 10 wherein $W^3$ is Bzl): This compound was prepared from 2-oxospiro [4.4]nonane-1,3-dione, described by M. N. Aboul-Enein et al., Pharm. Acta Helv., 55, 50 (1980), according to the asymmetric azidation method utilizing the Evan's auxiliary; see Evans et al., J. Amer. Chem. Soc., 112, 4011 (1990).

More explicitly, a 1.6M hexane solution of butyllithium (469 mL, 750 mmol) was added dropwise under an argon atmosphere to a solution of the chiral auxiliary, 4(S)-(1-methylethyl)-2-oxazolidinone, (96.8 g, 750 mmol) {described by L. N. Pridgen and J. Prol., J. Org. Chem, 54, 3231 (1989)} in dry THF at −40°. The mixture was stirred at −40° for 30 min and then cooled to −78°. 2-Oxospiro [4.4]nonane1,3-dione was added dropwise to the cooled mixture. The mixture was stirred at 0° for 1 h. Thereafter, a 20% aqueous solution of citric acid (600 mL) was added to the mixture. The organic phase was separated and the aqueous phase was extracted with EtOAc. The combined organic phases were washed with brine, dried ($MgSO_4$) and concentrated under reduced pressure to give 3-[2-(1-carboxycyclopentyl)-1-oxoethyl)}-4(S)-(1-methylethyl)-2-oxazolidinone as a pink solid (300 g).

The latter solid (ca 750 mmol) was dissolved in $CH_3CN$ (1 L). Benzyl bromide (89.2 mL, 750 mmol) and 1,8-diazabicyclo[5.4.0]undec-7-ene (112 mL, 750 mmol) were added to the solution. The mixture was stirred under argon for 16 h. The volatiles were removed under reduced pressure. The residue was dissolved in $H_2O$/EtOAc. The organic phase was separated, washed with a 10% aqueous solution of citric acid and brine, dried ($MgSO_4$) and concentrated under reduced pressure to give an oil. Crystallization of the oil from hexane/EtOAc gave the corresponding benzyl ester as a white solid (204 g, 73% yield).

A solution of the latter compound (70 g, 190 mmol) in dry THF (200 mL) was cooled to −78°. A 0.66M THF solution of potassium bis(trimethylsilyl)amide (286 mL, 190 mmol) containing 6% cumene was added over a period of 15 min to the cooled solution. The mixture was stirred at −78° for 45 min. A solution of 2,4,6-triisopropylbenzenesulfonyl azide (67 g, 220 mmol) in dry THF (100 mL) was added in one portion to the cold mixture, followed two minutes later by the addition of glacial acetic acid (50 mL, 860 mmol). The mixture was warmed and stirred at 35°–45° for 1 h. The volatiles were removed under reduced pressure. The yellow residue was triturated with hexane/EtOH (4:1, 1.7 L). The resulting white solid was collected on a filter. The filtrate was mixed with $SiO_2$ (230–240 mesh). Volatiles were removed under reduced pressure and the residual solid was dried at 35° under reduced pressure to remove cumene. The residual solid then was placed on a column of $SiO_2$. Elution of the column with hexane-EtOAc (9:1) and concentration of the eluent gave 3-{{2(S)-azido-1-oxo-2-{(1-{(phenylmethoxy)carbonyl}cyclopentyl}-ethyl}-4(S)-(1-methylethyl)-2-oxazolidinone (66 g, 86% yield).

A solution of the latter compound (13.4 g, 32.4 mmol) in THF/$H_2O$ (3:1, 608 mL) was cooled to 0°. Hydrogen peroxide/$H_2O$ (3:7, 16.3 mL, 141 mmol of $H_2O_2$) was added to the cooled solution, followed by the addition of LiOH.$H_2O$ (2.86 g, 68.2 mmol). The mixture was stirred at 0° for 45 min and then quenched with a 10% aqueous solution of sodium sulfite (400 mL). After NaHCO$_3$ (1.93 g) had been added, the mixture was concentrated under reduced pressure. The chiral auxiliary was recovered by continuous extraction (aqueous NaHCO$_3$/chloroform) for 20 h. Thereafter, the aqueous phase was cooled to 0° rendered acidic by the addition of concentrated HCl and then extracted with EtOAc. The extract was washed with brine, dried ($MgSO_4$) and concentrated under reduced pressure to give (S)-α-azido-1-{(phenylmethoxy) carbonyl}cyclopentaneacetic acid as a white solid (8.2 g, 84% yield). $^1$H NMR (CDCl$_3$) δ 7.40–7.28 (m, 5H), 5.12 (s, 2H), 4.55 (s, 1H), 2.30–2.20 (m, 1H), 2.05–1.95 (m, 2H), 0 1.8–1.6 (m, 5H).

(b) The title compound of this example: By following the coupling procedure of example 1 and using the hydrogen chloride salt of NH$_2$—(R)—CH(Et)CMe$_3$ of example 2 as the first reactant and (S)-α-azido-1-{(phenylmethoxy) carbonyl}cyclo-pentaneacetic acid of section (a) of this example as the second reactant, N-{1(R)-ethyl-(2,2-dimethylpropyl) }-(S)-α-azido-1-{(phenylmethoxy) carbonyl}cyclopentaneacetamide was obtained. Reduction of the latter compound with tin(II) chloride in MeOH according to the method of N. Maiti et al., Tetrahedron Letters, 27, 1423 (1986), followed by purification by chromatography (SiO$_2$, hexane-Et$_2$O, 1:1), gave the title compound of this example. $^1$H NMR (CDCl$_3$) δ 7.36–7.27 (m, 5H), 7.08 (d, J=10.5 Hz, 1H), 5.17 (d, J=12.3 Hz, 1H), 5.09 (d, J=12.3 Hz, 1H), 3.72 (s, 1H), 3.56 (ddd, J=10.5, 10.5, 2.5 Hz, 1H), 2.23–1.15 (m, 2H), 1.87–1.80 (m, 1H), 1.76–1.57 (m, 8H), 1.17–1.03 (m, 1H), 0.88 (s, 9H) and 0.86 (t, J=7.3 Hz, 3H).

EXAMPLE 4

Preparation of the Intermediate Boc-Tbg-CH$_2$—(R)—CH (CH$_2$C(O)CMe$_3$)C(O)OBzl (the compound of formula 2 wherein W$^1$ is Boc and W$^2$ is Bzl)

(a) Boc-Tbg-OMe (the compound of formula 3 wherein W$^1$ is Boc): A solution of Boc-Tbg-OH (68 g, 0.30 mol) in dry CH$_3$CN (0.5 L) was cooled to 0°. 1,8-Diazabicyclo [5.4.0]undec-7-ene (54 mL, 0.36 mol) was added over a period of 10 min to the cooled solution, followed by the addition of CH$_3$I (37 mL, 0.60 mol). The reaction mixture was stirred at room temperature (20°–22°) for 4 h and then concentrated under reduced pressure. The residue was partitioned between EtOAc and H$_2$O. The organic phase was washed with H$_2$O, an aqueous saturated solution of NaHCO$_3$ (2 X), and brine. Thereafter, the organic phase was dried (MgSO$_4$) and concentrated to afford a clear viscous liquid. This material was distilled bulb to bulb (oil pump vacuum, air bath temperature at 110°) to provide the desired product as a colorless oil (65 g, 88% yield). $^1$H NMR (CDCl$_3$) δ 5.10 (broad d, J=9.0 Hz, 1H), 4.10 (d, J=9.0 Hz, 1H), 3.72 (s, 3H), 1.44 (s, 9H), 0.96 (s, 9H).

(b) Boc-Tbg-CH$_2$-P(O)(OMe)$_2$ (the compound of formula 5 wherein W$^1$ is Boc): At –78° under a nitrogen atmosphere, a 5 L flask equipped with a mechanical stirrer, an addition funnel with jacket and a thermometer was charged with a solution of BuLi in hexane (3.60 mol, 361 mL of a 10N solution). A cold (–78°) solution of freshly distilled dimethyl methylphosphonate (391 mL, 3.60 mol) in dry THF (1 L) was added dropwise via the addition funnel over a 1 h period. The mixture was stirred at –78° for 30 min. A cold (–78°) solution of Boc-Tbg-OMe (111 g, 0.452 mol) in THF (0.5 L) was added dropwise over a 20 min period. The reaction was stirred at –78° for 45 min, and then allowed to warm to about –30° over a 30 min period. Following the sequential addition of glacial acetic acid (0.25 L) and H$_2$O (0.3 L), the mixture was extracted with EtOAc (1 L). The organic layer was washed with H$_2$O, a 10% aqueous solution of NaHCO$_3$ and brine, dried (MgSO$_4$) and concentrated. The resulting solid was triturated with hexane to give the desired phosphonate as a white powder with mp 84°–86° (144 g, 95% yield). $^1$H NMR (CDCl$_3$) δ 5.23 (broad d, J=9.0 Hz, 1H), 4.25 (d, J=9.0 Hz, 1H), 3.80 (d, J=11.4 Hz, 6H), 3.30 (dd, J=22.0, 14.6 Hz, 1H), 3.12 (dd, J =22.0, 14.6 Hz, 1H), 1.44 (s, 9H), 1.00 (s, 9H).

The phosphonate is used in section (d) of this example.

(c) HC(O)C(O)OBzl (the compound of formula 6 wherein W$^2$ is Bzl): Solid H$_5$IO$_6$ (49.3 g, 0.216 mol) was added portionwise to a solution of dibenzyl L-tartrate (70 g, 0.21 mol) in Et$_2$O (900 mL). The mixture was stirred for 2.5 h at room temperature and then filtered. The filtrate was dried (MgSO$_4$) and concentrated. The residual syrup was dissolved in hexane-Et$_2$O (2:3). The resulting milky solution was filtered through a pad of diatomaceous earth. The pad was washed with hexane-Et$_2$O (2:5). The combined filtrate and washing were concentrated to yield benzyl-glyoxylate as an oil (69.9 g, ~90% yield). H$^1$ NMR (CDCl$_3$) showed a mixture of aldehyde and hydrate form. Characteristic chemical shifts: δ 9.25 (s), 7.87–7.21 (m, 5H), 5.47–5.03 (m), 4.56 (broad s).

(d) The γ-keto-α,β-unsaturated ester Boc-Tbg-(E)-CH=CHC (O)OBzl (the compound of formula 7 wherein W$^1$ is Boc and W$^2$ is Bzl): A solution of Boc-Tbg-CH$_2$—P (O) (OMe)$_2$ (121 g, 0.359 mol), described in section (b) of this example, and triethylamine (0.10 L, 0.72 mol) in CH$_3$CN (0.7 L) was stirred under nitrogen for 10 min at room temperature. Thereafter, a solution of HC(O)C(O) OBzl (121 g, ~0.36 mol) in CH$_3$CN (0.15 L) was added over 30 min. The mixture was stirred for 24 h and then concentrated. The residue was dissolved in E$_2$O -hexane (2:1, 0.8 L). The solution was washed with a 10% aqueous solution of citric acid, a saturated solution of NaHCO$_3$ and brine, dried (MgSO$_4$) and concentrated. The resulting orange oil was passed through a silica gel pad (12×10 cm) using EtOAc-hexane (3:20) as the eluent. Concentration of the eluate gave the desired γ-keto-α,β-unsaturated ester as a yellow oil (112 g, 83% yield). $^1$H NMR (CDCl$_3$) δ 7.42–7.32 (m, 5H), 7.23 (d, J=15.9 Hz, 1H), 6.80 (d, J=15.9 Hz, 1H), 5.25 (s, 2H), 5.21 (broad d, J=8.9 Hz, 1H), 4.43 (d, J=8.9 Hz, 1H), 1.42 (s, 9H), 0.96 (s, 9H).

The γ-keto-α,β-unsaturated ester is used in section (f) of this example.

(e) CH$_2$=CHCH$_2$OC(O)CH$_2$C(O)CMe$_3$ (the compound of formula 8): A solution of lithium bis(trimethylsilyl)amide in THF (1N, 0.8 L) was cooled to –78°. A solution of allyl acetate (39 mL, 0.36 mol) in THF (40 mL) was added dropwise to the cooled solution. The mixture was stirred at –78° for 1 h. Thereafter, a solution of trimethyl-acetyl chloride (47 mL, 0.38 mol) was added dropwise and the resulting mixture was stirred for 25 min at –78°. Hexane (0.3 L) and an aqueous solution of HCl (3N, 0.6 L) were added to the mixture. The organic phase was separated and washed with a saturated aqueous solution of sodium bicarbonate, brine and water. The organic phase was dried (MgSO4), and concentrated to afford an orange oil. Distillation (bulb to bulb, air bath temperature of 60°, 0.25 Tor.) of the crude product gave desired ester as a colorless oil (62 g, 92% yield). $^1$NMR (CDCl$_3$) δ 6.02–5.87 (m, 1H), 5.35 (broad d, J=17.2 Hz, 1H), 5.25 (broad d, J=9.5 Hz, 1H), 4.63 (broad d, J=5.6 Hz, 2H), 3.59 (s, 2H), 1.19 (s, 9H).

(f) The Michael adduct, i.e. Boc-Tbg-CH$_2$—(R)—CH{CH (C(O)CMe$_3$)(C(O)OCH$_2$CH=CH$_2$)}C(O)OBzl (the compound of formula 9 wherein W$^1$ is Boc and W$^2$ is Bzl): Solid NaH (2.7 g of a 60% oil dispersion, 0.07 mol) was added over a 15 min period to a solution of CH$_2$=CHCH$_2$OC(O)CH$_2$C(O)CMe$_3$ (83.2 g, 0.452 mol) in THF (0.8 L). The reaction mixture was stirred at room temperature under an atmosphere of argon until all the solid dissolved (30 min). The homogeneous solution was cooled to −60° (solution temperature) and a solution of Boc-Tbg-(E)-CH=CHC (O)OBzl (170 g, 0.45 mol), described in section (d) of this example, in THF (0.5 L) was added slowly over a period of 45 min. Thereafter, the reaction mixture was stirred at −60° for 5 h. A 10% aqueous solution of citric acid was added and the mixture was allowed to warm to room temperature. The mixture was extracted with $Et_2O$. The organic phase was washed with a 5% aqueous solution of sodium bicarbonate and brine, dried ($MgSO_4$) and concentrated to afford an orange oil (250 g) which was used without further purification in the next reaction.

(g) Boc-Tbg-$CH_2$—(R)—CH ($CH_2$C (O) $CMe_3$) C (O)—OBzl: Pyrrolidine (56 mL, 0.54 mol) was added to a stirred solution of tetrakistriphenylphosphine palladium (O) (2.60 g, 2.25 mmol, 0.5% molar) in $CH_2Cl_{12}$ (250 mL) and $CH_3CN$ (250 mL) at 0° under an atmosphere of argon. The mixture was allowed to warm to room temperature. A solution of the Michael adduct from the preceding section (250 g, 0.45 mol) in $CH_2Cl_2$—$CH_3CN$ (200 mL:200 mL) was added to the mixture. After 3 h, the mixture was concentrated to yield an orange oil. The crude oil was dissolved in a mixture of $Et_2O$-hexane (1:1, 1 L). The solution was washed with a 10% aqueous solution of citric acid, 10% aqueous solution of sodium bicarbonate, and brine, dried ($MgSO_4$) and concentrated to give the title compound of this example as an orange oil (203 g, >90% yield). This material was used without further purification in example 5. A small sample was purified by $SiO_2$ chromatography. Elution with hexane-EtOAc (9:1) gave the pure title compound as a colorless oil. $[\alpha]_D^{25}$+11.5 (c =1.3, $CHCl_3$); $^1H$ NMR ($CDCl_3$) δ 7.38–7.28 (m, 5H), 5.10 (s, 2H), 5.07 (broad d, J=9.2 Hz, 1H), 4.08 (d, J=9.2 Hz, 1H), 3.38–3.31 (m, 1H), 3.09 (dd, J=18.8, 6.0 Hz, 1H), 2.94 (dd, J=18.4 6.1 Hz, 1H), 2.82 (dd, J=18.4, 6.1 Hz, 1H), 2.77 (dd, J=18.8, 6.0 Hz, 1H), 1.42 (s, 9H), 1.10 (s, 9H), 0.95 (s, 9H). The diastereoisomeric purity was assessed to be >35:1 by NMR; see P. L. Beaulieu et al., European patent application 560 267, published Sep. 15, 1993. In order to assess the enantiomeric purity of the title compound, the Boc protective group ($W^1$) was removed with 4N HCl in dioxane and the resulting amine was converted to a Mosher amide (see J. A. Dale et al., vide supra). By comparing results from a product prepared by the procedure of this example with results obtained with a racemic mixture of the title compound, the enantiomeric excess for said product was determined to be >96% by NMR and >99% by chiral column chromatography. The latter determination was performed by normal phase HPLC on a Chiracel® OD column from Daicel Chemical Industries Limited, Tokyo, Japan (U.S. distributor: Chiral Technologies Inc., Exton Pa, U.S.A.). EtOH-hexane (1:19) was the eluent and UV detection at 215 nmwas employed.

EXAMPLE 5

Preparation of the Intermediate Boc-Tbg-$CH_2$—(R)—CH($CH_2$C (O)$CMe_3$)C(O)OH (the compound of formula 14 wherein $W^1$ is Boc)

To a solution of the title compound of example 4 (171 g, 0.36 mol) in EtOH (1.4 L) was added 10% Pd/C (10 g). The resultant mixture was stirred vigorously under one atmosphere of hydrogen for 5 h. Thereafter, the reaction mixture was subjected to filtration through diatomaceous earth. The filtrate was concentrated under reduced pressure. The residue was dissolved in a saturated aqueous solution of $Na_2CO_3$. The aqueous solution was washed with hexane-$Et_2O$ (8:2), rendered acidic with citric acid and extracted with EtOAc. The extract was dried ($MgSO_4$) and concentrated. The orange residue was dissolved in $Et_2O$ and the resulting solution was passed through a silica gel pad (12×12 cm). Concentration gave the title compound of this example as a solid with mp 62°–65° (117 g, 84% yield). $^1H$ NMR ($CDCl_3$) δ 5.18 (d, J=8.8 Hz, 1H), 4.09 (d, J=8.8 Hz, 1H), 3.35–3.29 (m, 1H), 3.09 (dd, J=18.8, 6.3 Hz), 2.94 (dd, J=18.4, 6.3 Hz, 1H), 2.83 (dd, J=18.4, 6.3 Hz, 1H), 2.78 (dd, 18.8, 6.3 Hz, 1H), 1.43 (s, 9H), 1.14 (s, 9H), 0.96 (s, 9H).

EXAMPLE 6

Preparation of the Intermediate Boc-Tbg-$CH_2$—(R)—CH($CH_2$C (O)$CMe_3$)C(O)-Asp(cyPn)(Bzl)—NH—(R)—CH(Et)$CMe_3$(the compound of formula 15 wherein $R^5$ is Boc and $W^3$ is Bzl)

By following the coupling procedure of example 1 and using the title compound of example 3 as the first reactant and the title compound of example 5 as the second reactant, the title compound of this example is obtained. $^1H$ NMR ($CDCl_3$) δ 7.43–7.26 (m, 6H), 6.76 (d, J=10.0 Hz, 1H), 5.16 (s, 2H), 5.06 (d, J=8.9 Hz, 1H), 4.62 (d, J=8.9 Hz, 1H), 4.07 (d, J=8.9 Hz, 1H), 3.60 (ddd, J=10.0, 10.0, 2.5 Hz, 1H), 3.18–2.83 (m, 3H), 2.70 (dd, J=16.9, 4.1 Hz, 1H), 2.68–2.54 (m, 1H), 1.90–1.52 (m, 9H), 1.42 (s, 9H), 1.11 (s, 9H), 0.94 (s, 9H), 0.88 (s, 9H), 0.78 (t, J=7.3 Hz, 3H).

EXAMPLE 7

Preparation of the Intermediate Boc-(N-Me) Val-Tbg-$CH_2$—(R)—CH($CH_2$C(O)$CMe_3$)C(O)-Asp(cyPn)-(Bzl)—NH—(R)—CH (Et)$CMe_3$ (the compound of formula 18 wherein $R^5$ is Boc and $W^3$ is Bzl)

The title compound of example 6 (18.00 g, 0 24.8 mmol) was dissolved in 4M $HCl_1$/dioxane (125 mL). The mixture was stirred at room temperature for 45 min and then concentrated under reduced pressure to give H-Tbg-$CH_2$—(R)—CH($CH_2$C(O)$CMe_3$)—C (O)Asp(cyPn)(Bzl)-NH—(R)—CH(Et)$CMe_3$ in the form of its hydrochloric acid addition salt.

The latter salt was dissolved in $CH_2Cl_{12}$ (300 mL). The solution was washed successively with 10% aqueous $Na_2CO_3$ and brine. The organic phase was concentrated to give the corresponding free base as a clear oil (~17 g). The clear oil was dissolved in $CH_2Cl_2$ (200 mL). N-Methylmorpholine (7 mL, 70 mmol) and Boc-(N-Me)Val-OH (6.93 g, 30 mmol) were added to the solution. At this point, the free base was coupled with Boc-(N-Me)Val-OH according to the procedure of example 1 to give the title compound (18.8 g, 89% yield). $^1H$ NMR ($CDCl_3$) δ 7.40–7.29 (m, 6H), 6.83 (d, J=8.5 Hz, 1H), 6.77 (d, J=10 Hz, 1H), 5.17 (s, 2H), 4.62 (d, J=9.5 Hz, 1H), 4.55 (d, J=10 Hz, 1H), 4.28 (d, J=8 Hz, 1H), 3.64–3.56 (m, 1H), 2.97 (s, 3H), 3.05–2.50 (m, 7H), 2.33–2.23 (m, 1H), 1.91–1.56 (m, 15H), 1.34–1.14 (m, 7H), 1.11 (s, 9H), 1.05 (d, J=7 Hz, 3H), 0.95 (d, J=8.5 Hz, 3H), 0.90 (s, 9H), 0.77 (t, J=7 Hz, 3H).

EXAMPLE 8

Preparation of Some Representative Intermediates for the Elaboration of the N-Terminus of the Compound of Formula 1

(a) α(R)-Methylcyclohexanepropionic acid chloride: Under argon, a 1.6M hexane solution of burylithium (100 mL, 160 mmol) was added to a cooled solution (−30° to −40°) of 4(S)-(1-methylethyl)-2-oxazolidinone (20.7 g, 160 mmol), see L. N. Pridgen et al., J. Org. Chem., 54, 3231 (1989), in dry THF (200 mL). After 15 min, the mixture was cooled to −78° and propionyl chloride (14.2 mL, 163 mmol) was added. After 5 min at −78°, the reaction mixture was allowed to warm to 0°. The mixture then was treated with a saturated aqueous solution of $NaHCO_3$ (500 mL). The resultant mixture was extracted with EtOAc (2 X). The combined organic extracts were dried ($MgSO_4$) and concentrated to afford a yellow liquid. This material was purified by flash chromatography [$SiO_2$, eluent: EtOAc-hexane (1:10 to 1:4)] to provide (4S)-(1-methylethyl)-3-(1-oxopropyl)-2-oxazolidinone as a clear liquid (10.9 g, 74% yield). $^1H$ NMR (400 MHz, $CDCl_3$) δ 4.46–4.41 (m, 1H), 4.29–4.19 (m, 2H), 3.03–2.86 (m, 2H), 2.43–2.33 (m, 1H), 1.17 (t, J=7.3 Hz, 3H), 0.92 (d, J=7 Hz, 3H), 0.88 (d, J=7 Hz, 3H).

A solution of lithium hexamethyl-disilazane (LiHMDS, 1.0M in THF, 120 mL, 120 mmol) was added to dry THF (300 mL). The resultant solution was cooled to 0°. Meanwhile, a solution of (4S)-(1-methylethyl)-3-(1-oxopropyl)-2-oxazolidinone (20.9 g, 113 mmol) in dry THF (200 mL) was cooled to 0°, and then cannulated into the LiHMDS solution. After 30 min at 0°, benzyl bromide (13.4 mL, 113 mmol) was added. The resultant mixture was stirred at 0° for 2 h and then allowed to warm to room temperature. The mixture was treated with 10% aqueous citric acid and then extracted with EtOAc (2 X). The combined organic extracts were washed with brine, dried ($MgSO_4$) and concentrated to provide a yellow oil mixed with a solid. This material was purified by flash chromatography [$SiO_2$, eluent: EtOAc-hexane (1:10 to 1:3)] to provide 4(S)-(1-methylethyl)-3-(2(R)-methyl-1-oxo-3-phenylpropyl)-2-oxazolidinone as a clear pale yellow liquid (26.8 g, 86% yield). $^1H$ NMR ($CDCl_3$) δ 7.29–7.24 (m, 4H), 7.22–7.16 (m, 1H), 4.45–4.41 (m, 1H), 4.26–4.13 (m, 3H), 3.13 (dd, J=13, 7.5 Hz, 1H), 2.64 (dd, J=13, 7.5 Hz, 1H), 2.22–2.12 (m, 1H), 1.16 (d, J=6.5 Hz, 3H), 0.84 (d, J=7 Hz, 3H), 0.61 (d, J=7 Hz, 3H).

To a cooled solution (0°) of the latter oxazolidine derivative (26.7 g, 97.0 mmol) in THF (9500 mL) and $H_2O$ (1.5 L) was added a 30% aqueous solution of hydrogen peroxide (55 mL, 0.5 mol), followed by the addition of a solution of $LiOH \cdot H_2O$ (8.67 g, 200 mmol) in $H_2O$ (15 mL). The resultant mixture was vigorously stirred for 1 h at 0°. A solution of $Na_2SO_3$ (100 g) in $H_2O$ (700 mL) and solid $NaHCO_3$ (20 g) were added sequentially. After 5 min, the THF was removed under reduce pressure. The residual aqueous solution was washed with $CH_2Cl_{12}$ (3 X). The aqueous phase was rendered acidic with 10% aqueous $HCl_1$ and extracted with $Et_2O$ (3 X). The combined $Et_2O$ extracts were washed with brine, dried ($MgSO_4$) and concentrated to afford α(R)-methylbenzenepropionic acid as a clear liquid (12.8 g, 81% yield). $^1H$ NMR ($CDCl_3$) δ 7.33–7.19 (m, 5H), 3.10 (dd, J=13.5, 6.5, 1H), 2.83–2.74 (m, 1H), 2.79 (dd, J=13.5, 8 Hz, 1H), 1.20 (d, J=7 Hz, 3H).

A mixture of α(R)-methylbenzenepropionic acid (3.0 g, 18 mmol) and 5% rhodium on alumina (800 mg) in methanol (100 mL) was shaken under 40 p.s.i. of $H_2$ on a Parr hydrogenation apparatus. After 15 h, the mixture was filtered through diatomaceous earth and concentrated to afford α(R)-methylcyclohexanepropionic acid as a clear liquid (2.4 g, 77%). $^1H$ NMR ($CDCl_3$) δ 2.62–2.53 (m, 1H), 1.79–1.59 (m, 6H), 1.38–1.16 (m, 5H), 1.17 (d, J=7 Hz, 3H), 0.95–0.83 (m, 2H).

To a solution of α(R)-methylcyclohexane-propionic acid (2.4 g, 14 mmol) in dry $CH_2Cl_{12}$ (30 mL) was added DMF (1 drop) and oxalyl chloride (2 g, 15 mmol). After 2 h at room temperature, the mixture was concentrated. The residue was dissolved in $Et_2O$ (10 mL). This solution was filtered. The filtrate was concentrated to provide α(R)-methylcyclohexanepropionic acid chloride as a clear yellow liquid (2.6 g, 98% yield). $^1H$ NMR (400 MHz, $CDCl_3$) 3.02–2.91 (m, 1H), 1.80–1.63 (m, 6H), 1.39–1.10 (m, 5H), 1.28 (d, J=7 Hz, 3H), 0.99–0.85 (m, 2H). This material was used without further purification in the coupling reaction described in the following example.

(b) α(S)-(1-Methylethyl)cyclohexanepropionic acid chloride: By following procedure (a) of this example but replacing propionyl chloride with 3-methylbutanoyl chloride, α(S)-(1-methylethyl)-cyclohexane propionic acid is obtained. $^1H$ NMR ($CDCl_3$) δ 2.27 (ddd, J=10.5, 7, 3.5 Hz, 1H), 1.91–1.80 (m, 2H), 1.73–1.55 (m, 5H), 1.35–1.08 (m, 5H), 0.98–0.77 (m, 2H), 0.97 (d, J=7 Hz, 3H), 0.96 (d, J=7 Hz, 3H). Thereafter, the latter compound was converted to its corresponding acid chloride in the same manner as described in section (a) of this example.

(c) α(R),β(R)-Dimethylcyclohexanepropionic acid: Oxalyl chloride (2.9 mL, 33.3 mmol) and then 2 drops of dimethylformamide were added to a solution of β(R)-methylbenzenepropionic acid (4.0 mL, 26.1 mmol). The mixture was stirred at room temperature for 2h, and then evaporated to dryness under reduced pressure to give the corresponding acid chloride (i.e. first reactant), which was used hereinafter.

In a separate preparation, a solution of 4(R)-(1-methylethyl)-2-oxazolidinone (3.06 g, 23.7 mmol) in dry THF (30 mL) was cooled to −50°. Under argon, a 1.6M hexane solution of butyllithium (14.8 mL, 23.7 mmol) was added dropwise to the cooled solution of the oxazolidinone derivative. After 15 min at −78°, a solution of the first reactant in dry THF (10 mL) was added. The reaction mixture was stirred at −70° for 30 minutes and then allowed to warm to room temperature over a 45 min period. The mixture was quenched with excess 10% aqueous $NH_4Cl$. Thereafter, the THF was removed under reduced pressure and the resulting concentrate was dissolved in EtOAc. The solution was washed with 5% aqueous $NaHCO_3$ (2 X) and brine (2 X), dried ($MgSO_4$) and concentrated to give an oil. The oil was purified by flash chromatography [$SiO_2$, hexane-EtOAc (43:7)] to yield (4R)-(1-methylethyl)-3-(3(R)-methyl-1-oxo-3-phenylpropyl)- 2-oxazolidinone (6.1 g, 93% yield).

A solution of potassium hexamethyldisilazane (KHMDS, 0.692M in THF, 23.3 mL, 16.1 mmol) was added to dry THF (50 mL) and the mixture was cooled to −78° A solution of the preceding oxazolidine derivative (4.03 g, 14.7 mmol) in dry THF (40 mL) was cooled to −78°. The latter solution was then cannulated into the KHMDS solution. The mixture was stirred at −78° for 1 h. Methyl iodide (1.75 mL, 28.1 mmol) was added. After being stirred at −78° for 2.5 h more, the reaction mixture was warmed to room temperature. The mixture was quenched with 10% aqueous citric acid. After the THF was removed under reduced pressure, the resulting concentrate was dissolved in EtOAc. The solution was washed with 10% aqueous citric acid (2 X), 5% aqueous NaHSO$_3$ and brine, dried (MgSO$_4$) and concentrated to dryness. The residue was purified by flash chromatography [SiO$_2$, eluent: hexane-EtOAc (42:8)] to yield 4(R)-(1-methylethyl)-3-(2(R),3(R)-dimethyl-1-oxo-3-phenylpropyl)-2-oxazolidonone (2.84 g, 67% yield).

Reaction of the latter oxazolidinone derivative (2.80 g, 9.69 mmol) with 30% aqueous hydrogen peroxide (5.5 mL, 48.5 mmol) in the presence of LiOH.H$_2$O (0.81 g, 19.3 mmol), followed by reduction of the resulting α(R),β(R)-dimethyl-benzenepropionic acid with 5% rhodium on alumina (1.76 g) in MeOH, according to the procedure of section (a) of this example, afforded α(R),β(R)-dimethylcyclohexanepropionic acid (1.74 g, 96% yield from the latter oxazolidinone derivative). $^1$H NMR (CDCl$_3$) 2.63 (qd, J=6.5, 6.5 Hz, 1H), 1.80–1.71 (m, 4H), 1.68–1.63 (m, 2H), 1.29–0.91 (m, 6H), 1.08 (d, J=7 Hz, 3H), 0.84 (d, J=6.5 Hz, 3H). Thereafter, the latter compound was converted to its corresponding acid chloride in the same manner as described in section (a) of this example.

EXAMPLE 9

Preparation of (3-Cyclohexyl-2(R)-methyl-1-oxopropyl)-(N—Me) Val-Tbg-CH$_2$—(R)—CH(CH$_2$C(O)CMe$_3$)—C(O)-Asp(cyPn)-NH—(R)—CH(Et)CMe$_3$ (the compound of formula 1 wherein R$^1$=H and R$^2$=Me).

The title compound of example 7 (18.8 g, 21.98 mmol) was dissolved in 4M HCl$_1$/dioxane (200 mL). The solution was stirred at room temperature for 7 h and then concentrated. The resulting residue was dissolved in CH$_2$Cl$_2$ (350 mL). The solution was washed with 10% aqueous Na$_2$CO$_3$ and then brine. Concentration of the solution provided H—(N—CH$_3$)Val-Tbg-CH$_2$—(R)—CH(CH$_2$C(O)—CMe$_3$) C(O)-Asp(cyPn)-NH—(R)—CH(Et)CMe$_3$ (~17 The latter compound was dissolved in CH$_2$Cl$_2$ (200 mL). After the addition of N-methylmorpholine (2.5 mL, 25 mmol) and α(R)-methylcyclohexane-propionic acid chloride, the mixture was stirred at room temperature for 1.5 h. Thereafter, the mixture was washed with 10% aqueous Na$_2$CO$_3$, 10% aqueous citric acid and brine, dried (MgSO$_4$) and concentrated to give the corresponding protected carbonyl derivative of the title compound of this example (12.5 g, 63% yield), i.e. the compound of formula 21 wherein R$^1$ is hydrogen, R$^2$ is methyl and W$^3$ is Bzl.

The latter derivative (12.2 g, 13.5 mmol) was subjected to hydrogenolysis [10% Pd(OH)$_2$/C (1.3 g), 1 atmosphere of H$_2$, MeOH (150 mL), 1 h]. Thereafter, charcoal was added to the reaction mixture and the resulting suspension was filtered through a glass microfiber filter and diatomaceous earth. The filtrate was concentrated under reduced pressure to yield the title compound as a fine white powder (10.7 g, 97% yield). Mp 115°–116°; $^1$H NMR (d$_6$-DMSO) δ 8.31 (d, J=7 Hz, 0.25H), 8.23 (broad, J=10 Hz, 1H), 7.86 (d, J=8.5 Hz, 0.75H), 6.93 (overlap, d, J=10 Hz, 1H), 4.91 (overlap, d, J=10 Hz, 1H), 4.70 (d, J=10 Hz, 0.75H), 4.22 (d, J=10.5 Hz, 0.25H), 4.16 (overlap, d, J=8.5 Hz, 1H), 3.45–3.37 (m, 1H), 3.24–3.15 (m, 1H), 2.96 (s, 2.25H), 2.88 (s, 0.75H), 2.88–2.50 (m, 5H), 2.19–2.00 (m, 2H), 1.70–1.44 (m, 14H), 1.44–0.62 (m, 47H, characteristic singlets at 1.04, 0.88 and 0.87); FAB MS (m/z): 817.6 (M+H)$^+$.

By following the procedure of this example but replacing α(R)-methylcyclohexanepropionic acid chloride with α(S)-(1-methylethyl)-cyclohexanepropionic acid chloride, then {3-cyclohexyl-2(S)-(1-methylethyl)-1-oxopropyl}-(N-Me) Val-Tbg-CH$_2$—(R)—CH(CH$_2$C(O)CMe$_3$)C(O)-Asp(cypn)-NH—(R)—CH (Et)CMe$_3$ was obtained. $^1$H NMR (d$_6$-DMSO) δ 8.23 (d, J=10 Hz, 1H), 8.01 (d, J=8 Hz, 1H), 6.93 (d, J=10 Hz, 1H), 4.92 (d, J=10 Hz, 1H), 4.80 (d, J=11 Hz, 1H), 4.13 (d, J=8.5 Hz, 1H), 3.40–3.37 (m, 1H), 3.23–3.16 (m, 1H), 3.00 (s, 3H), 2.84–2.56 (m, 4H), 2.53–2.48 (m, 1H, overlap with Me's of DMSO), 2.18–2.08 (m, 1H), 2.06–2.02 (m, 1H), 1.73–1.42 (m, 15H), 1.39–1.28 (m, 1H), 1.24–1.00 (m, 4H), 1.04 (s, 9H), 0.92–0.77 (m, 15H), 0.90 (s, 9H), 0.87 (s, 9H), 0.64 (t, J=7 Hz, 3H); FAB MS (m/z): 845 (M+H)$^+$.

Again, by following the procedure of this example but replacing α(R)-methylcyclohexane-propionic acid chloride with α(R), β(R)-dimethyl-cyclohexanepropionic acid chloride, then (3-cyclohexyl-2 (R), 3 (R)-dimethyl-1-oxopropyl)-(N-Me) Val-Tbg-CH$_2$—(R)—CH (CH$_2$C(O)CMe$_3$)C(O)-Asp (cyPn)-NH—(R)—CH (Et) CMe$_3$ was obtained. $^1$H NMR (d6-DMSO) δ 8.23 (d, J=9.5 Hz, 0.9H), 8.16 (d, J=5 Hz, 0.1H), 7.84 (d, J=8.5 Hz, 1H), 6.98 (broad, 0.1H), 6.94 (d, J=10 Hz, 0.9H), 4.96 (broad, 0.1H), 4.91 (d, J=10 Hz, 0.9H), 4.70 (d, J=11.5 Hz, 0.9H), 4.23 (d, J=10 Hz, 0.1H), 4.16 (d, J=8.5 Hz, 0.9H), 3.96 (d, J=5 Hz, 0.1 H), 3.42–3.37 (m, 1H), 3.24–3.16 (m, 1H), 2.96 (s, 2.7H), 2.90 (s, 0.3H), 2.83–2.50 (m, 5H)2.19–2.02 (m, 2H), 1.73–1.35 (m, 15H), 1.20–0.96 (m, 6H), 1.04 (s, 9H), 0.91–0.87 (m, 6H), 0.89 (s, 9H), 0.87 (s, 9H), 0.79 (d, J=7 Hz, 3H), 0.77 (d, J=7 Hz, 3H), 0.65 (t, J=7 Hz, 3H); FAB MS (m/z): 831 (M+H)$^+$.

EXAMPLE 10

Inhibition of Herpes Simplex Virus (HSV-1) Ribonucleotide Reductase a) Preparation of Enzyme HSV-1 ribonucleotide reductase (partially purified) was obtained from quiescent BHK-21/C113 cells infected with strain F HSV-1 virus at 10 plaque forming units/cell as described by E. A. Cohen et al., J. Gen. Virol., 66, 733 (1985).

b) Assay

The assay described by P. Gaudreau et al., J. Biol, Chem., 262, 12413 (1987), is used to evaluate the capability of the compounds of formula 1 to inhibit HSV-1 ribonucleotide reductase activity. The assay results are expressed as the concentration of the compound producing 50% of the maximal inhibition (IC$_{50}$) of enzyme activity. The number of units of the enzyme preparation used in each assay was constant, based on the specific activity of the enzyme preparation. The results are relative to the activity obtained in control experiments without the test compound and represent the means of four assays that varied less than 10% with each other.

The following TABLE I illustrates the assay results obtained for exemplified compounds of formula 1.

TABLE I

Compound of the Formula

[Chemical structure diagram]

| wherein R¹ and R² are as designated herein below | IC$_{50}$ μM |
|---|---|
| R¹ =H and R² =Me | 0.147 |
| R¹ =H and R² =CHMe$_2$ | 0.123 |
| R¹ and R² =Me | 0.191 |

EXAMPLE 11

Inhibition of Herpes Simplex Virus (HSV-1) Replication in Cell Culture

Assay

BHK-21 cells clone 13 (ATCC CCL10) were incubated for two days in 850 cm$^2$ roller bottles (2×10$^7$ cells/bottle) with alpha-MEM medium (Gibco Canada Inc., Burlington, Ontario, Canada) supplemented with 8% (v/v) fetal bovine serum (FBS, Gibco Canada, Inc.). The cells were trypsinized and then transferred to fresh media in a 96-well microtiter plate at a density of 50,000 cells per well in 100 μL. The cells were incubated at 37° for a period of 6 hours to allow adhesion to the plate. The cells then were washed once with 100 μL of alpha-MEM supplemented with 0.5% FBS (v/v) and incubated with 100 μL of the same media for 3 days. After this period of serum starvation, the low serum media was removed. The cells were washed once with 100 μL BBMT and incubated for two hours in 100 μL of the same media. {Note: BBMT medium is described by P. Brazeau et al., Proc. Natl. Acad. Sci. U.S.A., 79, 7909 (1980).}

Thereafter, the cells were infected with HSV-1 strain F or KOS (multiplicity of infection =0.05 PFU/cell) in 50 μL of BBMT medium. Following one hour of virus absorption at 37°, the media was removed and the cells were washed with BBMT (2×100 μL). The cells were incubated with or without 100 μL of the appropriate concentration of test reagent in BBMT medium. After 24 hours of incubation at 37°, the extent of viral replication was determined by an ELISA assay; for instance, the following assay that detects the late glycoprotein C of HSV-1.

Cells were fixed in a microtiter plate with 100 μL of 0.063% glutaraldehyde in phosphate buffered saline for 30 minutes at room temperature. The microtiter plate was then washed once with casein blocking solution and blocked with 200 μL of the same solution for one hour at room temperature. Thereafter, 100 μL of mAB CII recognizing HSV-1 gC envelope protein [see E. Trybala et al., Journal of General Virology, 75, 743 (1994)] was added to each well for two hours at room temperature. The plate was washed three times with phosphate buffered saline containing 0.05% polyoxyethylene (20) sorbitan monooleate. The cells were and incubated with 100 μL of sheep anti-mouse IgC horseradish peroxidase for one hour at room temperature in the dark.

The plate then was washed three times with 200 μL of the above-noted phosphate buffer saline preparation, and then once with 0.1M sodium citrate (pH 4.5). Thereafter, 100 μL of orthophenylenediamine dihydrochloride (OPD, Gibco, Canada Inc.) was added to each well. The plate was agitated on a microplate shaker for 30 minutes in the dark. Color development was monitored at 450 nm using a microplate spectrophotometer.

SAS was used to calculate % inhibition of viral replication and to generate ECI$_{50}$ values.

Results

The following TABLE II provides examples of the results obtained when compounds of formula 1 were evaluated according to the cell culture assay (HSV-1 strain F) of this example.

TABLE II

Compound of the formula

[Chemical structure diagram]

| wherein R¹ and R² are as designated herein below | EC$_{50}$ μM |
|---|---|
| R¹ =H and R² =Me | 0.4 |
| R¹ =H and R² =CHMe$_2$ | 0.2 |
| R¹ and R² =Me | 0.2 |

EXAMPLE 12

Synergistic Combinations

The synergistic action between the title compound of example 9 and acyclovir (ACV) against HSV-1 was demonstrated by evaluating the two agents, each alone and then in various combinations in the cell culture assay, using strain KOS of HSV-1 and applying the isobole method to the results obtained in these studies; see J. Sühnel, J. Antiviral Research, 13, 23 (1990) for a description of the isobole method. The results are illustrated in accompanying FIG. 1.

More explicitly with reference to the isobole method, this method requires experimental data generated for the two test compounds, each alone and in different combinations. In this way selected concentrations of the title compound of example 9 (EC$_5$, EC$_{10}$, EC$_{20}$ and EC$_{30}$) were added to a given concentration of ACV and the EC$_{50}$'s were evaluated as described previously. For these experiments, the EC$_5$, EC$_{10}$, EC$_{20}$ and EC$_{30}$ of the title compound of example 9 (i.e. the test compound) were derived from inhibition curves previously obtained. An isobologram is generated using for the Y axis a value termed FEC$_{60}$ (ACV) (which is the ratio of the concentration of ACV required to inhibit HSV replication by 60% in the presence of a fixed concentration of the test compound to the concentration required in the absence of the test compound). This is plotted against a term representing the ratio of the fixed concentration of the test compound to the concentration of the test compound that reduced inhibition of HSV replication in the absence of ACV (the X axis).

Equations

X axis:
$$\frac{[\text{the fixed concentration of the test compound added}]}{EC_{60} \text{ of the test compound alone}}$$

Y axis:
$$FEC_{60}(ACV) = \frac{EC_{60}(ACV + X\,\mu M \text{ of the test compound})}{EC_{60}(ACV \text{ alone})}$$

The following TABLE III is illustrative of results obtained when combinations of ACV and the title compound of example 9 (TC) were evaluated for their antiherpes activity against HSV-1. The virus strain and the multiplicity of infections (MOI) employed were HSV-1 KOS strain (MOI =0.05 PFU/cell).

TABLE III

SYNERGISTIC STUDIES OF ACYCLOVIR (ACV) AND THE TITLE COMPOUND OF EXAMPLE 9 (TC) AGAINST HSV-1

| COMPOUNDS | $EC_{50}$ $(\mu M)^1$ |
|---|---|
| Compound Alone | |
| ACV[2] | 6.95 |
| TC | 0.473 |
| Synergistic Studies | |
| ACV + 0.05 µM of TC | 6.3 |
| ACV + 0.1 µM of TC | 3.2 |
| ACV + 0.15 µM of TC | 1.79 |
| ACV + 0.2 µM of TC | 1.79 |
| ACV + 0.3 µM of TC | 1.0 |
| ACV + 0.4 µM of TC | 0.5 |

[1]Stock solutions of the title compound of example 9 were filtered through a 0.22 µM membrane and then the concentration of the compound in the filtered solution was determined by HPLC.
[2]Acyclovir was obtained from Burroughs Wellcome Inc., Kirkland, Quebec, Canada.

Note: In the preceding studies of TABLE III, the inhibition of the HSV replication was observed at concentrations significantly below the cytotoxic levels for the test compounds as determined by the cytotoxicity assay of F. Denizot and R. Lang, J. Immunol. Methods, 89, 271 (1986).

The results of TABLES III show that, on combining the title compound of example 9 with acyclovir, a proportional lowering of the $EC_{50}$ of acyclovir is effected as the ratio of the concentrations of the title compound of example 9 is increased. Hence, these synergistic studies demonstrate that the compounds of formula 1 are able to potentiate the antiherpes activity of acyclovir against HSV-1.

We claim:
1. A compound of formula 1

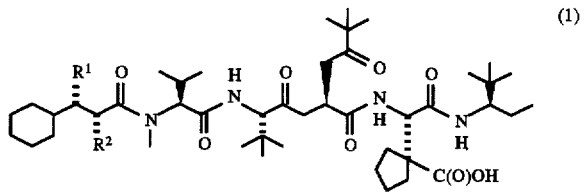

wherein $R^1$ is hydrogen or (1–4C)alkyl and $R^2$ is (1–4C) alkyl; or a therapeutically acceptable salt thereof.

2. The compound of formula 1 as defined in claim 1 wherein $R^1$ hydrogen or methyl and $R^2$ is methyl, ethyl, 1-methylethyl or propyl; or a therapeutically acceptable salt thereof.

3. The compound of formula 1 as defined in claim 2 wherein $R^1$ is hydrogen and $R^2$ is methyl, ethyl or 1-ethylmethyl; or a therapeutically acceptable salt thereof.

4. A pharmaceutical composition comprising a compound of formula 1 as defined in claim 1, or a therapeutically acceptable salt thereof, and a pharmaceutically acceptable carrier.

5. A cosmetic composition comprising a compound of formula 1 as defined in claim 1, or a therapeutically acceptable salt thereof, and a physiologically acceptable carrier suitable for topical application.

6. A method for treating a herpes viral infection in a mammal comprising the step of administering to the mammal an anti-herpes virally effective amount of the pharmaceutical composition according to claim 4.

7. A method for inhibiting the replication of a herpes virus comprising the step of contacting the virus with a herpes viral ribonucleotide reductase inhibiting amount of a compound of formula 1 as defined in claim 1 or a therapeutically acceptable salt thereof.

8. The compound of formula 1 as defined in claim 3 selected from the group consisting of (3-cyclohexyl-2(R)-methyl-1-oxopropyl)-(N—Me) Val-Tbg-CH$_2$—(R)—CH (CH$_2$—C(O)CMe$_3$)C(O)-Asp(cyPn)-NH—(R)—CH (Et) CMe$_3$, {(3-cyclohexyl-2 (S)-(1-methylethyl)-1-oxopropyl }-(N—Me) Val-Tbg-CH$_2$—(R)—CH (CH$_2$C(O)CMe$_3$)C(0)-Asp(cyPn)-NH—(R)—CH(Et) CMe$_3$, and (3-cyclohexyl-2 (R),3(R)-dimethyl-1-oxopropyl)-(N—Me) Val-Tbg-CH$_2$—(R)—CH(CH$_2$C(0)CMe$_3$)C(0)-Asp(cyPn)-NH—(R)—CH (Et) CMe$_3$.

9. A pharmaceutical composition comprising an anti-herpes virally effective amount of a compound of formula 1 as defined in claim 8, or a therapeutically acceptable salt thereof, and a pharmaceutically acceptable carrier.

10. A cosmetic composition comprising a compound of formula 1 as defined in claim 8, or a therapeutically acceptable salt thereof, and a physiologically acceptable carrier suitable for topical application.

11. A method for treating a herpes viral infection in a mammal comprising the step of administering to the mammal an anti-herpes virally effective amount of the pharmaceutical composition according to claim 9.

12. A method for inhibiting the replication of a herpes virus comprising the step of contacting the virus with a herpes viral ribonucleotide reductase inhibiting amount of a compound of formula 1 as defined in claim 8 or a therapeutically acceptable salt thereof.

13. A pharmaceutical composition comprising a pharmaceutically or veterinarily acceptable carrier, and an effective amount of a combination comprising an antiviral nucleoside analog, or a therapeutically acceptable salt thereof, and a compound of formula 1 as defined in claim 1, or a therapeutically acceptable salt thereof.

14. The pharmaceutical composition according to claim 13 wherein the nucleoside analog is a compound of formula 22

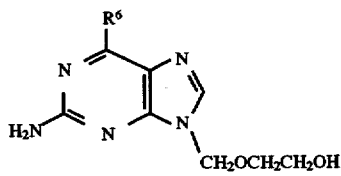

wherein $R^6$ is hydrogen, hydroxy or amino, or a therapeutically acceptable salt thereof.

15. The pharmaceutical composition according to claim 13 wherein the antiviral nucleoside analog is selected from the group consisting of penciclovir, famciclovir and valacyclovir.

16. A method for treating a herpes viral infection in a mammal comprising the step of administering to the mammal an anti-herpes virally effective amount of a combination of an antiviral nucleoside analog, or a therapeutically acceptable salt thereof, and a compound of formula 1 according to claim 1, or a therapeutically acceptable salt thereof.

17. The method according to claim 16 wherein the nucleoside analog and the compound of formula 1 are administered sequentially or simutaneously.

18. The method according to claim 16 wherein the combination is administered topically.

19. The method according to claim 16 wherein the antiviral nucleoside analog is selected from the group of acyclovir, 6-deoxyacyclovir, 2,6-diamino-9-{(2-hydroxyethoxy)methyl}purine, penciclovir, famci-clovir and valacyclovir.

20. The method according to any one of claims 6, 11 or 16 wherein the herpes viral infection is a herpes simplex virus type 1 or a herpes simplex virus type 2 infection.

21. A process for preparing a compound of formula 1 as defined in claim 1, or a therapeutically acceptable salt thereof, comprising the steps of:

(a) reacting a free N-terminal compound of formula 19

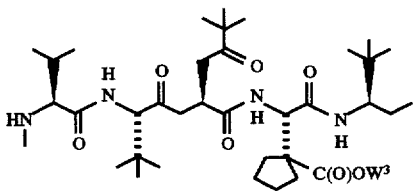

wherein $W^3$ is a carboxyl protective group with an acid chloride formula 20

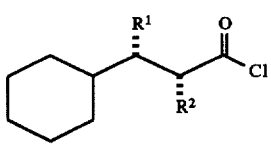

wherein $R^1$ and $R^2$ are as defined in claim 1 to obtain a corresponding protected carboxyl derivative of formula 21

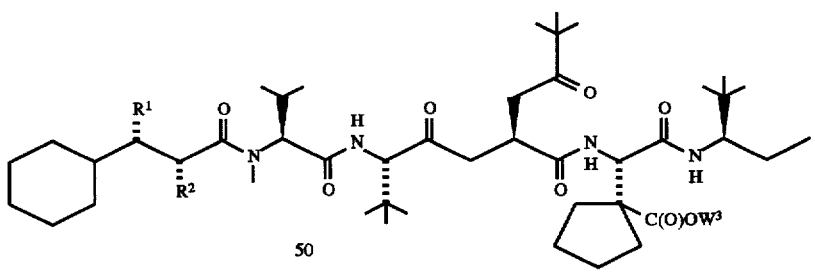

wherein $R^1$, $R^2$ and W3 are as defined in this claim, and (b) deprotecting the latter derivative of formula 21 to obtain the corresponding compound of formula 1.

22. The process according to claim 21, further comprising the step of transforming the compound of formula 1 into a therapeutically acceptable salt thereof.

* * * * *